United States Patent [19]
Good et al.

[11] Patent Number: 5,028,425
[45] Date of Patent: Jul. 2, 1991

[54] SYNTHETIC VACCINE AGAINST *P. FALCIPARUM* MALARIA

[75] Inventors: Michael F. Good; Sanjai Kumar, both of Rockville; Jay A. Berzofsky, Bethesda; Louis H. Miller, Chevy Chase, all of Md.

[73] Assignee: The United States of America as represented by the Department of Health and Human Services, Washington, D.C.

[21] Appl. No.: 216,088

[22] Filed: Jul. 7, 1988

[51] Int. Cl.$^5$ ............... A61K 39/00; A61K 37/02
[52] U.S. Cl. ...................... 424/88; 530/325; 530/326; 530/350; 514/13
[58] Field of Search ............... 424/88; 530/325, 326, 530/350; 514/13

[56] References Cited

U.S. PATENT DOCUMENTS 4,707,357 11/1987 Dame et al. ............... 424/88
4,769,235 9/1988 Schlesinger et al. ............... 424/88

OTHER PUBLICATIONS

Dame et al., "Structure of the Gene Encoding the Immuno-Dominant Surface Antigen on the Sporozoite of Flu Human Molaria Parasite *Plasmodium Falciparum*", *Science, vol. 225, pp. 593-599, Aug. 1984.*

Primary Examiner—Margaret Moskowitz
Assistant Examiner—Abdel A. Mohamed
Attorney, Agent, or Firm—Mishrilal Jain

[57] ABSTRACT

A purified peptide which induces proliferation or activation of cytotoxic T cells specifically against circumsporozoite protein of *P. falciparum* is described. The peptide has an amino acid sequence KPKDELDYEN-DIEKKICKMEKCS in single letter amino acid code.

2 Claims, 5 Drawing Sheets

SYNTHETIC VACCINE AGAINST P. FALCIPARUM MALARIA

TECHNICAL FIELD

The present invention is related generally to antimalarial vaccines. More particularily, the present invention is related to providing a synthetic peptide which induces proliferation or activation of cytotoxic T cells having specificity against circumsporozoite protein for protection against *Plasmodium falciparum* infection.

BACKGROUND OF INVENTION

Control of malarial disease has been achieved to a certain degree in various parts of the world. Yet, complete eradication of malaria still remains to be achieved. A vaccine providing protective immunity would, therefore, be a desirable tool for checking disease caused by malarial infection.

SUMMARY OF INVENTION

It is, therefore, an object of the present invention to provide a substantially pure peptide which induces proliferation of cytotoxic T lymphocytes (CTL) that specifically recognize native circumsporozoite (CS) protein and kill the cells infected with malaria sporozoites.

It is another object of the present invention to provide a vaccine, comprising immunogenic amount of the purified peptide of the present invention to induce proliferation of the CTLs that specifically recognize CS protein and kill cells expressing CS protein.

It is a further object of the present invention to provide a method of controlling malarial infection, comprising inducing protective immunity in a host susceptible to malarial infection by inoculating said host with immunogenic amount of the vaccine of the present invention.

Other objects and advantages will become evident from the following detailed description of the present invention.

DETAILED DESCRIPTION OF THE INVENTION

The above and various other objects and advantages of the present invention are achieved by a synthetic peptide which resembles the immunodominant epitope on CS protein and which elicits CTL response. This epitope is located within residues 368-390 of the CS protein.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed herein are standard methodologies well known to one of ordinary skill in the art. The term "substantially pure" as used herein means as pure as can be obtained by standard purification techniques.

FIGS. 1-4 described the various materials and methods employed and the results obtained in accordance with the present invention.

Figure 1:
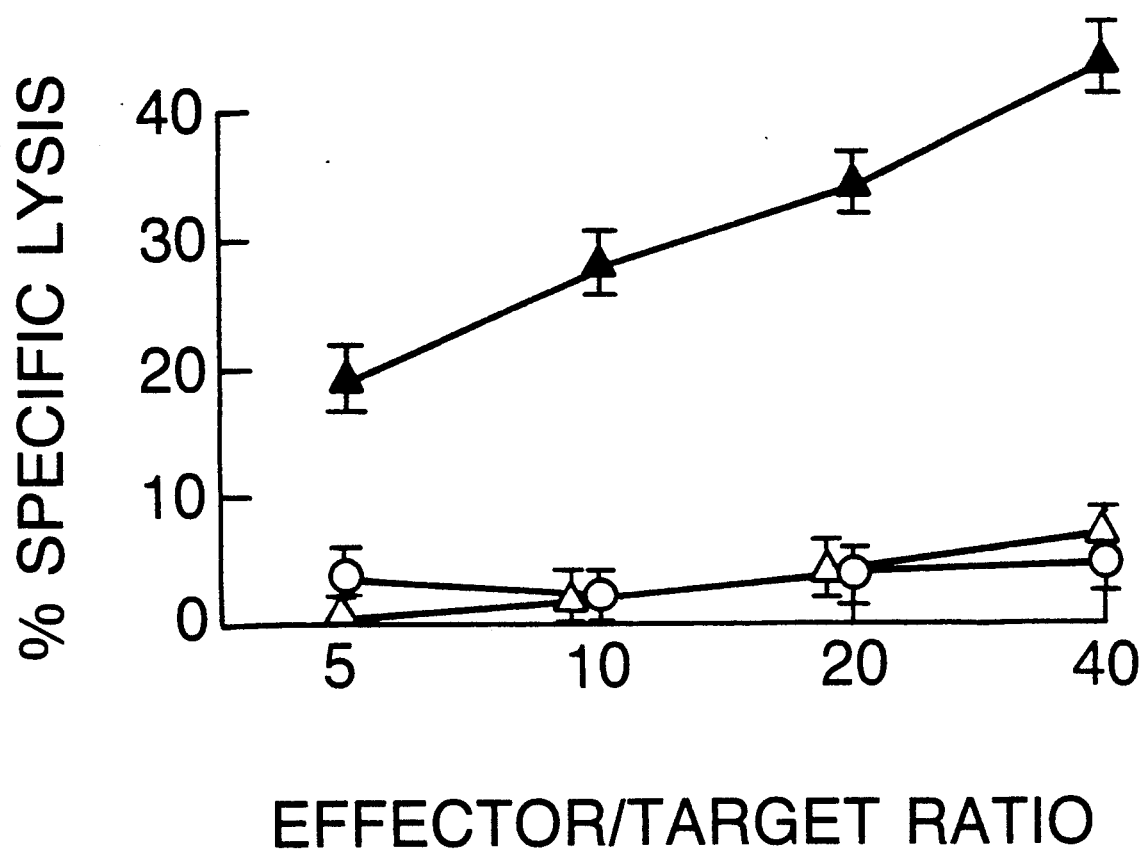

FIG. 1 presents data showing that the CS protein is a target for CTL. B10BR mice (H-5k) were immunized intravenously with $10^7$ pfu of a CS-recombinant vaccinia virus. Three weeks later, spleens were taken and $5 \times 10^6$ spleen cells were incubated with $2 \times 10^5$ CS-transfected L cells treated with mitomycin C (50 μg/ml, 30 min) in 2 ml RPMI 1640 medium containing 10% fetal calf serum, $5 \times 10^{-5}$M 2-mercaptoethanol and penicillin and streptomycin. After 7 days culture, cells were harvested, counted and incubated for 6 hours at various effector/target ratios with 5000 $^{51}$Cr-labelled CS-transfected L cells, ▲ ; pSV2-neo transfected L cells (L-28), △; or untransfected, uninfected L cells, O. Percent specific lysis was determined as:

$$\frac{(\text{experimental cpm} - \text{medium control cpm}) \times 100}{(\text{detergent released cpm} - \text{medium control cpm})}$$

The spontaneous release values (medium control cpm/detergent released cpm) for all targets in all tests were very similiar with a mean value of 16.8% +/− 1.1% (S.E.M.). Error bars on this and other figures represent +/− standard error of mean (triplicate assays). Unstimulated spleen cells from unimmunized mice did not kill target cells.

Mouse L cells (H-2k) were transfected with the CS gene of the 7G8 clone of *P. falciparum* by standard calcium phosphate precipitation. Briefly, the CS gene containing the entire coding sequence was cloned at ECORI site into the expression vector pcEXV-3. This expression vector contains SV40 enhancer, early promoter, splice signals 5' of the gene insert as well as a polyadenylation signal downstream. The rest of the sequences are derived from pBR 322. L cells ($5 \times 10^5$ cells per 60 mm petri dish) were co-transfected in 1 ml with 10 μg of purified plasmid DNA and 3 μg pSV2neo DNA. The calcium phosphate/DNA precipitate was left on the cells overnight. The following day, the original medium was replaced with fresh medium and left for an additional 24 h and then transfectants selected in 2 mg/ml G418 (Geneticin; Gibco) for 1 week. Finally, stable transfected cells were grown in the presence of 200 μg/ml G418. Single colonies of transfectants were obtained by limiting dilution and screened by standard immunofluorescence technique for the expression of CS protein.

Figure 2:
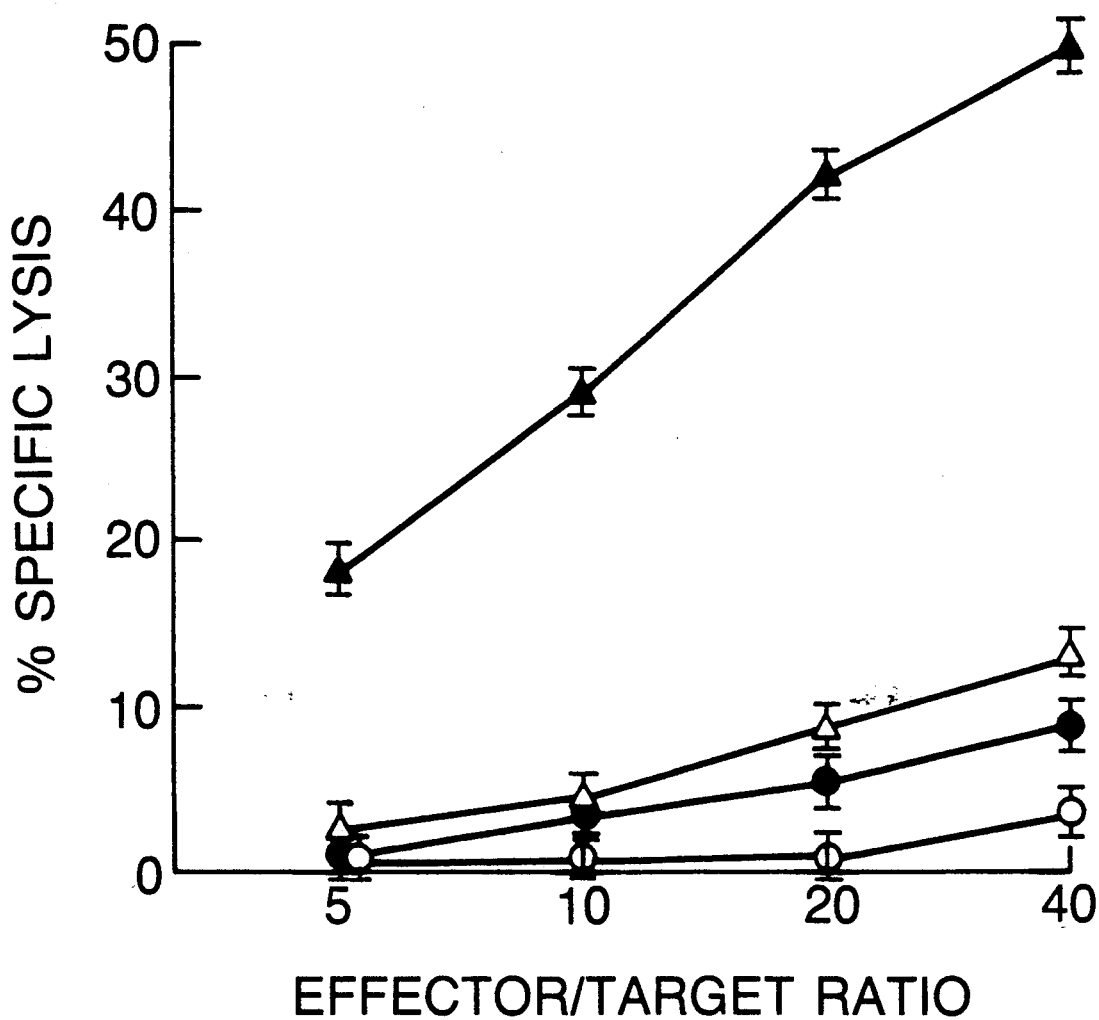

FIG. 2 demonstrates sporozoite stimulation of CS specific CTL. B10.BR mice were immunized intravenously with $10^5$ (irradiated 10000 Rad) *P. falciparum* sporozoites (7G8 clone) ▲ , △). Control mice were not immunized (▲ , ○). After 3 weeks, mice were sacrificed and spleens taken. Spleen cells were then stimulated in vitro with CS-transfected L cells as described in FIG. 1. After 6 days, killing of CS-transfected L cells (▲ , ●) and untransfected L cells (△, ○) was measured. The data show the results obtained.

Figure 3A:
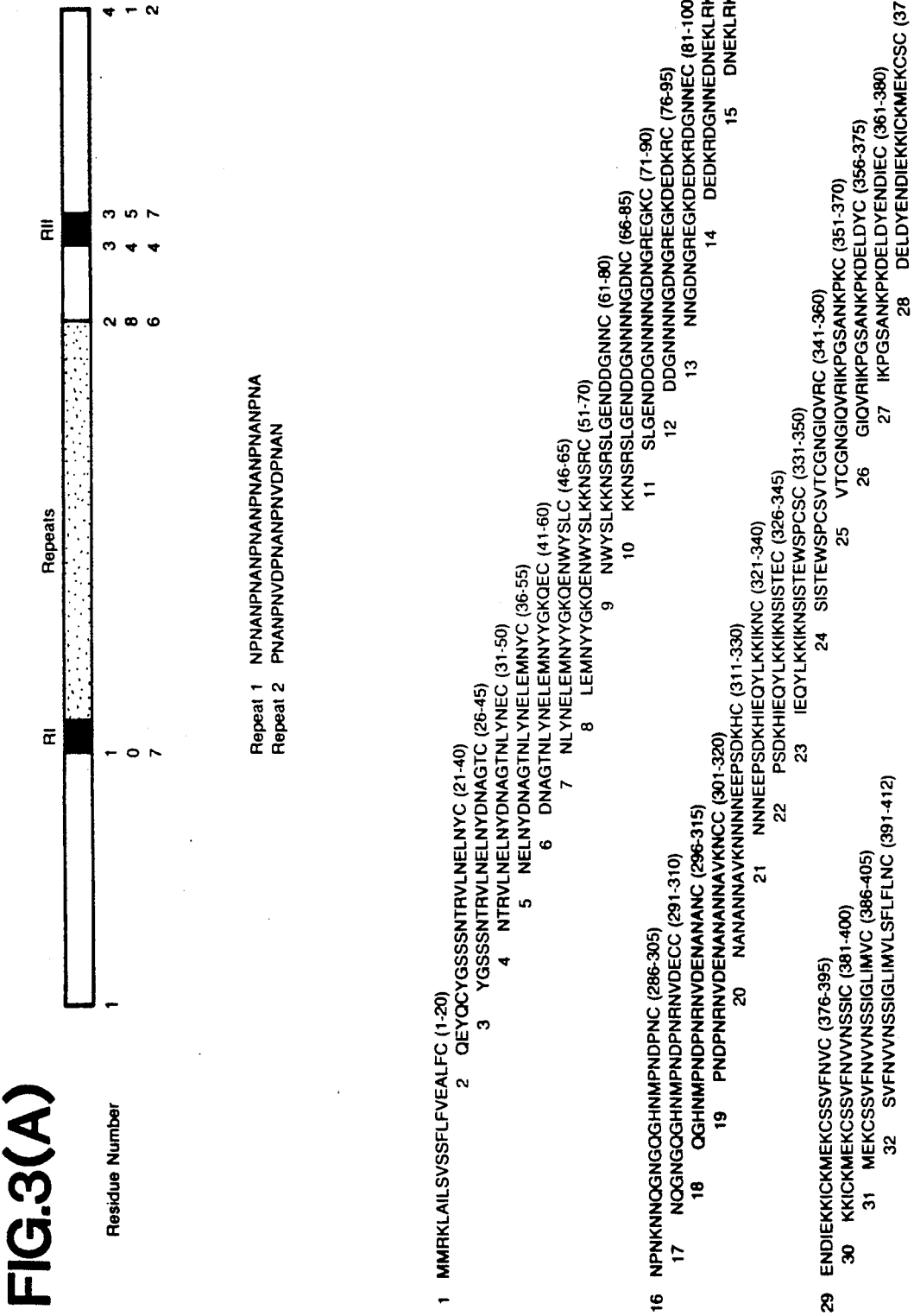

FIG. 3a is a schematic illustration of the CS protein and description of the peptides. RI (Region I) and RII (Region II) refer to areas of strong homology between CS proteins from different species of malaria. The sequences of the 34 peptides tested were those described by Dame et al, Science 225:593-599, 1984. Each peptide has a carboxyl terminal cysteine which is not part of the protein sequence. The numbers in brackets refer to the residue number. Peptides were produced as described by Houghten, PNAS (USA) 82; 5131-5135., and desalted prior to use. They were checked for purity by reversed phase HPLC. The peptides were nontoxic. It is noted, however, that the peptides could be produced FIG. 3b defines CD8 epitope on CS protein. Spleen cells from CS-vaccinia-immunized B10.BR mice were stimulated in vitro with CS-transfected L cells as described in FIG. 1. Putative CTL were then incubated with untransfected L cells at an effector/target ratio of 10/1 for 6 hours in the presence of various concentrations of peptide 28 (●). There was no specific lysis of L cells by peptide 28 in the absence of CTL (○), i.e., the peptide was not toxic to these cells. The killing of the transfected L cell was also measured, at an effector/target ratio of 10/1 (▲).

Anti-CS protein-specific CTL did not kill L cells in the presence of any of the other 33 peptides at concentrations of 1, 10, 20, or 100 g/ml. Peptide 28 did not sensitize L cells to killing by irrelevant allospecific CTL (C57Bl/10 anti-BALB/c).

Figure 4:
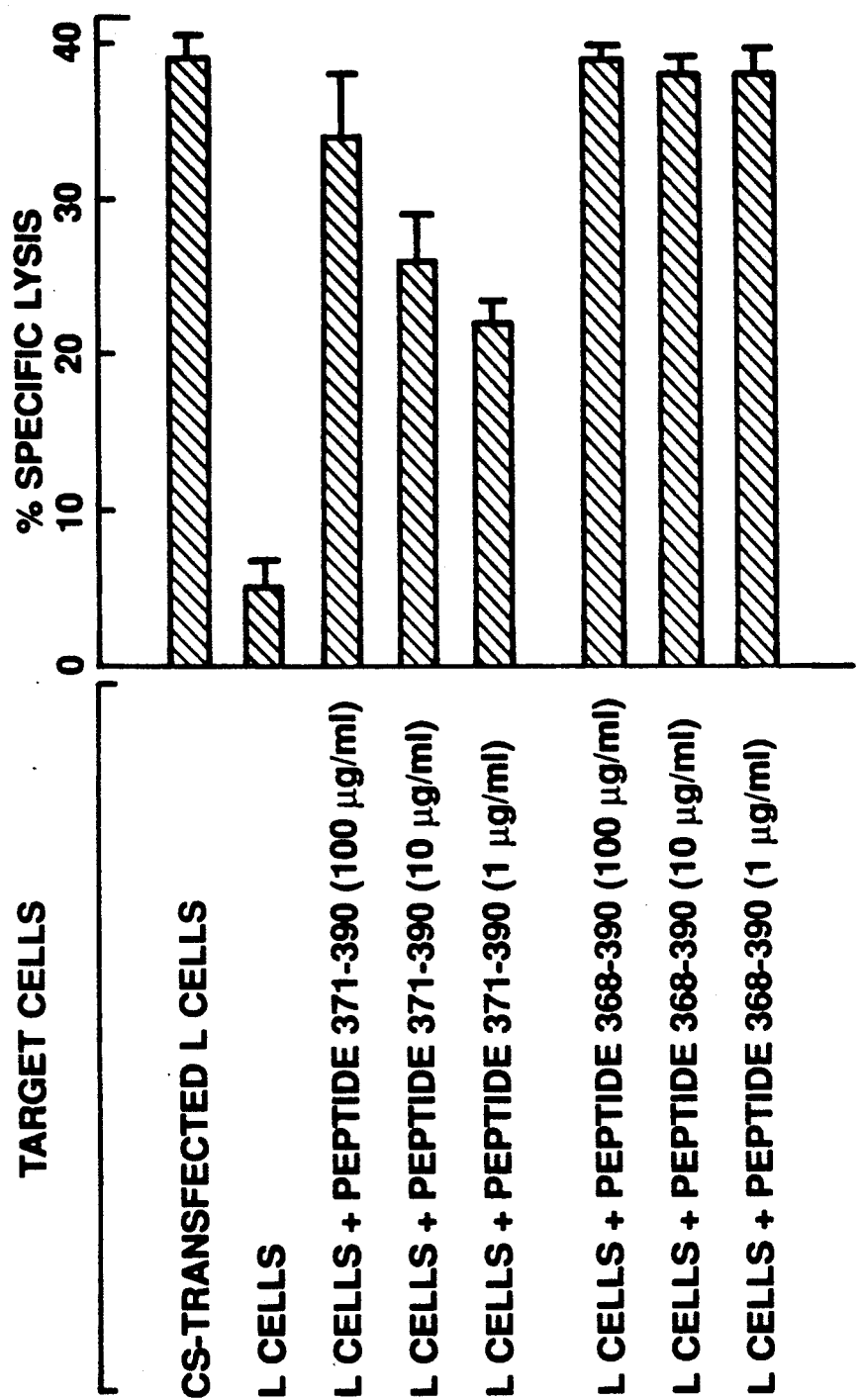

FIG. 4 presents evidence that the CTL epitope is located within residues 368–390 of CS protein. Spleen cells from CS-vaccinia immunized B10.BR mice were stimulated in vitro with CS-transfected L cells as described in FIG. 1. Cultured cells were then incubated at an effector/target ratio of 30/1 for 5 hours in the presence of various targets: CS-transfected L cells; untransfected L cells; untransfected L cells incubated overnight with peptide (as indicated) at 100 μg/ml, then washed and re-incubated with peptide at 100, 10, or 1 μg/ml during the cytotoxicity assay. It was found that overnight incubation (about 12 to 16 hours) with peptide increased the degree of specific killing (not shown). Similar results were obtained at an effector/target ratio of 10/1. Peptides 370–390 and 368–390 were not toxic to L cell and peptide 368–390 was not recognized by vaccinia-specific CTL (not shown).

It is known that malaria is initiated following innoculation of sporozoites by a mosquito. Sporozoites enter hepatocytes and develop for a period as exoerythrocytic or hepatic stage parasites. Vaccination with irradiated malaria sporozoites can protect the host from mosquito-induced infection. In vivo depletion of CD8+ T cells, a subset that contains Class I-restricted cytotoxic T lymphocytes (CTL), as well as lymphocytes with a supressor function, in a sporozoite-immunized animal can completely abrogate immunity. It is believed that CTL from immune animals recognize the infected hepatocytes and kill the intrahepatic parasites. The evidence presented herein demonstrates that the circumsporozoite (CS) protein covering the sporozoite contains the target epitopes for CD8+ T cell-mediated immunity. B10.BR mice immunized with sporozoites or with recombinant vaccinia virus expressing the CS protein of *Plasmodium falciparum* contain CTL that specifically kill L cells (fibroblasts) transfected with the gene encoding the same CS protein. The peptide epitope from the CS protein that is recognized by CTL from this strain of mice was found to be from a variant strain of the CS protein.

As shown herein above, specific killing of the CS gene-transfected L cells was observed indicating that the CS protein did contain one or more epitopes recognized by CTL (FIG. 1). These CTL also recognized the other CS-transfected L cell clone as well as CS-recombinant vaccinia infected L cells, but not, wild type vaccinia infected L cells (data not shown). It was further observed that CS-specific CTL were sensitive to anti-CD8 monoclonal antibody and complement. Following incubation of CS-specific CTL with anti-CD8 (19/178 clone) followed by complement, there was 3.8% specific lysis of CS-transfected targets at an effector/target ratio of 10/1, compared with specific lysis of 29% when CTL were incubated with complement alone. Lysis of untransfected L cells was 3.2% following complement treatment, and 0.12% following treatment with anti-CD8 and complement. Because the CS protein was only expressed cytoplasmically by the transfectants, these data give further confirmation to the findings that the entire protein containing CTL epitopes need not be expressed on the cell surface for CTL-target cell interaction.

It should be noted that while stimulation of the CTL by virus encoded proteins is well documented, heretofore there was no direct evidence of stimulation of CTL by malaria parasites. Therefore, as shown in the data presented herein, B10.BR mice were immunized intravenously with freshly prepared 7G8 sporozoites, and three weeks after immunization mice were sacrificed and spleen cells were stimulated in vitro with CS gene-transfected L cells. After seven days culture, specific lytic activity was demonstrated against transfected L cells (FIG. 2). Spleen cells from unimmunized B10.BR mice could not be stimulated to generate specific lytic activity against transfected L cells (FIG. 2). Thus, it was concluded that sporozoites stimulate CS-specific CTL in vivo.

Figure 3B:
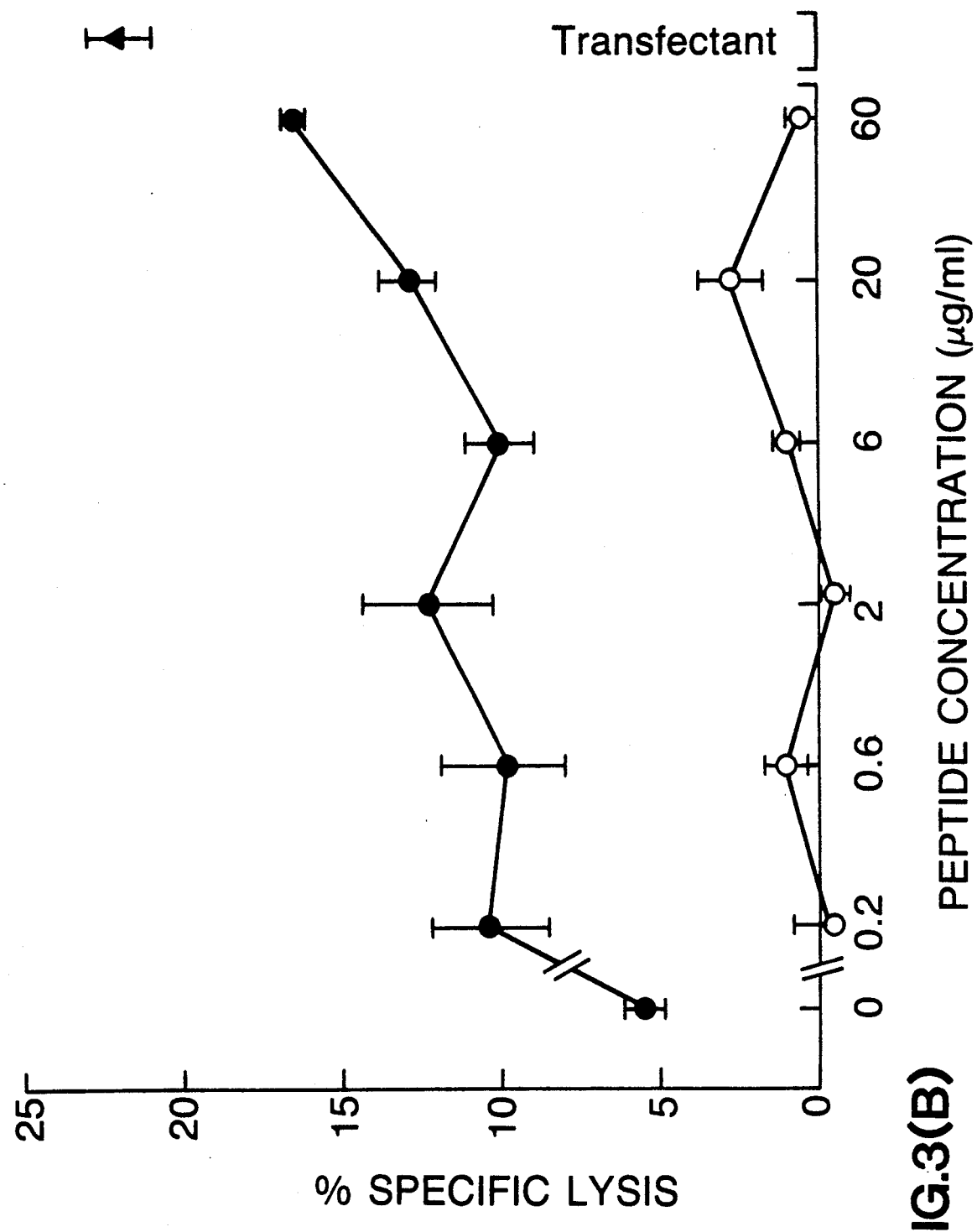

To determine the epitope recognized by CS protein-specific CTL, a series of overlapping peptides spanning the entire CS protein were constructed (FIG. 3a). (See also Good et al, PNAS, USA, 85:1199–1203, 1988). CTL were then incubated with L cells in the presence of each of the peptides, and lysis determined by $^{51}$Cr release procedure as described, for example, by Townsend et al, Cell, 44:959, 1986. Peptides were tested at concentrations of 1, 10, 20, and 100 μg/ml. Only one peptide (#28) was recognized by CTL. A dose-response study demonstrated significant killing at concentrations as low as 0.2 μg/ml (FIG. 3b). However, specific killing by B10.BR anti-CS protein CTL in the presence of this peptide was not as great as killing of the transfected L cells, possibly indicating that peptide 28 does not contain the full T site. Thus, peptides 370–390 and 368–390 were made (lacking the additional carboxy-terminal cysteine present on peptide 28) and tested for recognition by B10.BR anti-CS protein CTL. L cells incubated with peptide 368–390 were killed at the same level as CS-transfected cells, and more efficiently than L cells incubated with peptide 370–390 (FIG. 4) indicating that the full T site was contained within residues 368–390. The observation that CTL recognized peptide 368–390 to the same degree as the transfectant, gave further indication that B10.BR CS-specific-CTL recognize only this single epitope on the CS protein.

The results further demonstrate that malaria sporozoites induce CS-protein-specific CTL, and that in B10.BR mice the CTL response is restricted to a single peptide epitope from a variant region of the protein (residues within 368–390 region of the CS protein). Since sporozoites can prime CTL in vivo, it is postulated without being bound to any specific theory that the sporozoites must generate stimulator cells in the host to induce CTL, and these stimulators are equivalent to targets as well. Thus, generation of CTL by injection of sporozoites indicates that sporozoite infected cells in vivo are targets of CTL, thereby providing protection from sporozoite infection.

A synthetic vaccine for protection against *P. falciparun* is now made possible by a pharmaceutical composition, comprising immunogenic amount of the isolated, substantially pure peptide, constituting residues 368-390 (or modified equivalent thereof) of CS protein containing about 23 amino acid residues in functionally equivalent sequence. The term "modified equivalent" as used herein means that the 368-390 epitope can be changed by any means such as deletion, addition, derivatization, substitution and the like so that a peptide of at least an equivalent function is obtained. The composition may, of course, include pharmaceutically acceptable carriers or vehicles, such as non-toxic, sterile buffers and physiological saline, adjuvants, preservatives or sterilants as are well known to one of ordinary skill in the art. The present invention now also provides a method for inducing protective immunity against *P. falciparum* malaria, comprising inoculating a host susceptible to *P. falciparum* malaria, with immunogenic amount of peptide 368-390 or modified equivalent thereof to induce production of CTLs sufficient to kill cells infected with *P. falciparum* sporozoites. Booster inoculations at periodic intervals, as necessary, may be administered to maintain immunogenic or cytocidal level of CTLs.

It is understood that the examples and embodiments described herein are for illustrative purposes only and that various modifications or changes in light thereof will be suggested to persons skilled in the art and are to be included within the spirit and purview of this application and scope of the appended claims.

We claim:

1. A synthetic peptide consisting essentially of amino acid sequence KPKDELDYENDIEKKICKMEKCS from amino to carboxyl end in single letter amino acid code.

2. A composition, comprising an immunogenic amount of the peptide of claim 1 sufficient to induce production of cytotoxic T-lymphocytes to kill cells infected with *P. falciparum* sporozoites and a pharmaceutically acceptable carrier.

* * * * *